US00PP08569P

United States Patent [19]

Warrinerm, deceased

[11] Patent Number: Plant 8,569

[45] Date of Patent: Feb. 1, 1994

[54] HYBRID TEA ROSE PLANT NAMED 'JACLIN'

[75] Inventor: William A. Warriner, deceased, late of Tustin, Calif., by Alene B. Warriner, legal representative

[73] Assignee: Bear Creek Gardens, Inc., Medford, Oreg.

[21] Appl. No.: 883,102

[22] Filed: May 14, 1992

[51] Int. Cl.[5] ..... A01H 5/00

[52] U.S. Cl. ..... Plt./20

[58] Field of Search ..... Plt. 20

*Primary Examiner*—Howard J. Locker

*Attorney, Agent, or Firm*—Klarquist, Sparkman, Campbell, Leigh and Whinston

[57] ABSTRACT

A hybrid tea rose having non-fading bright red flowers of high centered tea flower form which have a long vase life. The plant has a vigorous, upright growth habit and long stems.

1 Drawing Sheet

The present invention relates to a new and distinct variety of rose plant of the Hybrid tea class which was originated by me by crossing the varity JACsho, U.S. Plant Pat. No. 4,851, with the variety Mister Lincoln, U.S. Plant Pat. No. 2,370.

The primary objective of this breeding was to produce a new rose variety having the bright red flower color and good flower form of the female parent JACsho combined with the vigor and upright well branched habit of the male parent. The objective was substantially achieved along with other desirable improvements as evidenced by the following unique combination of characteristics which are outstanding in the new variety and which distinguish it from its parents, as well as from all other varieties of which I am aware:

1. Very bright red non-fading flower color;
2. High centered flower form;
3. Vigorous upright growth habit;
4. Long cutting stems;
5. Very good vase life.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JACsho, U.S. Plant Pat. No. 4,851.

*Pollen parent.*—Mister Lincoln, U.S. Plant Pat. No. 2,370.

Classification:

*Botanical.*—*Rosa hybrida.*

*Commercial.*—Hybrid tea.

FLOWER

Observations made from specimens grown in a garden environment in Somis, Calif. from August–October, 1991.

Blooming habit: Recurrent.

Bud:

*Size.*—1½" when the petals start to unfurl.

*Form.*—Long, pointed ovoid.

*Color.*—When sepals first divide, bud color is Red Group 45B. When half blown, the upper sides of the petals are Red Group 45B; and the lower sides of the petals are Red Groyup 45B.

*Sepals.*—Color: Green Group 138C. Surface texture: Covered in many fine hairs. There are three lightly appendaged sepals. There are two unappendaged sepals with hairy edges.

*Receptacle.*—Color: Green Group 137D. Shape: Funnel. Size: Small, ⅜"×⅜". Surface: Smooth.

*Peduncle.*—Length: Medium, 5½". Surface: Smooth. Color: Medium green. Strength: Stiff, erect.

Bloom:

*Size.*—Medium. Average open size is 4".

*Borne.*—Singly.

*Stems.*—Long, 18–22".

*Form.*—When first open: High centered. Permanence: Retains its form to the end, outer petals curl back.

*Petalage.*—Number of petals under normal conditions: 30–35.

*Color.*—The upper side of the petals is Red Group 45B. The reverse side of the petals is Red Group 45B. The base of petals has a small yellow half moon at the point of attachment, ⅛"×⅛". The major color on the upper side is Red Group 45B.

*Variegations.*—Occasional white streak on the guard petals.

*Discoloration.*—The general tonality at the end of the first day: No change. At the end of the third day: No change.

*Fragrance.*—Slight.

Petals:

*Texture.*—Thick.

*Shape.*—Round to slightly deltoid.

*Form.*—Tips slightly recurved, edges slightly quilled.

*Arrangement.*—Imbricated, with few petaloids in the center.

*Persistence.*—Drop off cleanly.

*Lastingness.*—On the plant: Long, 6–7 days. As a cut flower: Long, 8 days.

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Light yellow with red blush near the stigma.

*Stigmas.*—Color: Greenish white.

Form: Bush.

Growth: Very vigorous; upright; branching.

Foliage:

*Number of leaflets on normal mid-stem leaves.*—5 or 7.

*Size.*—Large, 6"×4".

*Quantity.*—Abundant.

*Color.*—New foliage; Red. Old foliage: Dark green.

Leaflets:

*Shape.*—Broadly oval to pointed oval.

*Texture.*—Upper side: Leathery, glossy.

*Edge.*—Serrated.

*Serration.*—Single, small.

*Petiole rachis.*—Color: Green.

*Petiole underside.*—With prickles.

*Stipules.*—Medium; serrated.

*Disease resistance.*—Susceptible to mildew but resistant to rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: ordinary. On laterals from main canes: Ordinary.

*Form.*—Medium, hooked downward.

*Color when young.*—Red.

Small prickles:

*Quantity.*—On main stalks: None. On laterals: Few.

It is claimed:

1. A new and distinct variety of rose plant of the hybrid tea class, substantially as herein shown and described, characterized particularly as to novelty by the unique combination of its excellent non-fading bright red flower color, its high centered hybrid tea flower form, its long vase life as a garden cut flower, its vigorous, upright growth habit and its long stems.

* * * * *

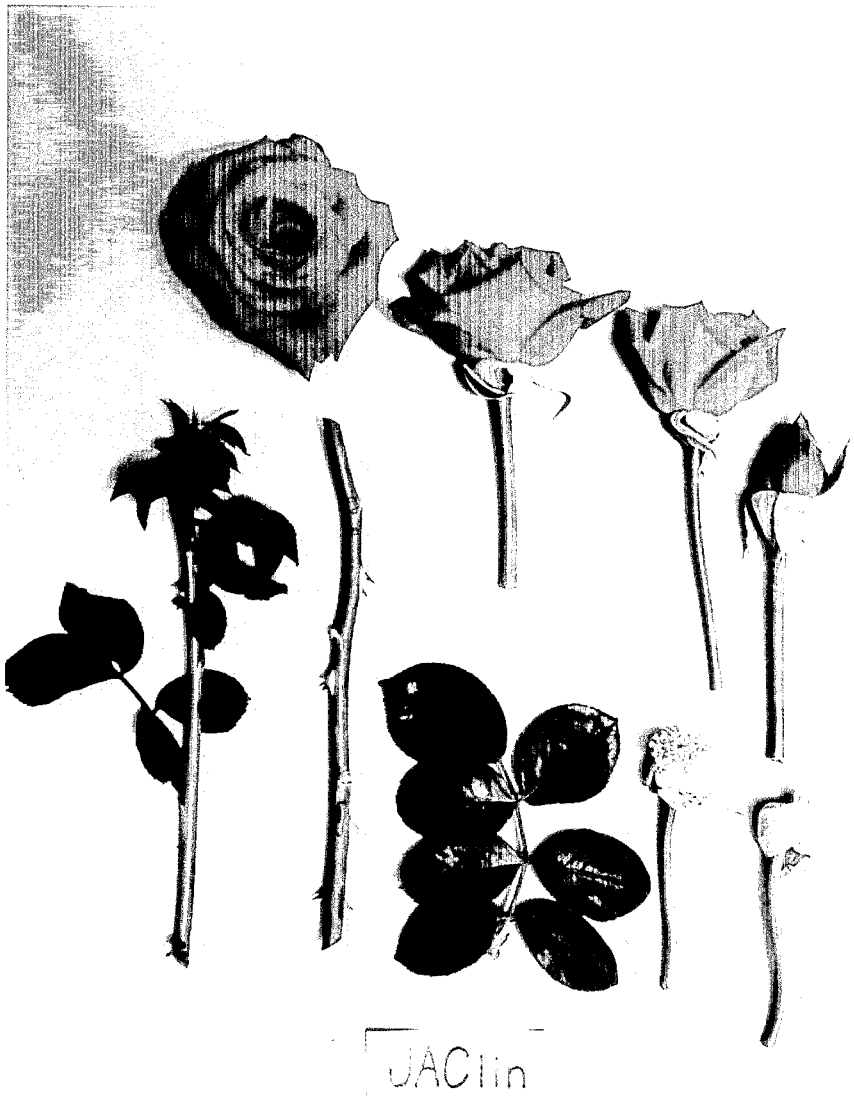
JACIin